United States Patent [19]

Jackman et al.

[11] Patent Number: 4,659,819

[45] Date of Patent: Apr. 21, 1987

[54] PRODUCTION OF S-SUBSTITUTED ISOTHIOUREAS

[75] Inventors: Dennis E. Jackman, Prarie Village; Dietmar B. Westphal, Lenexa, both of Kans.; Thomas Schmidt, Ginsterweg, Fed. Rep. of Germany

[73] Assignees: Mobay Corporation, Pittsburgh, Pa.; Bayer Aktiengesellschaft, Leverkusen, Fed. Rep. of Germany

[21] Appl. No.: 632,132

[22] Filed: Jul. 18, 1984

[51] Int. Cl.$^4$ .................. C07D 253/06; C07D 251/38; C07D 239/38

[52] U.S. Cl. .................... 544/182; 544/219; 544/223; 544/318; 544/316; 544/315; 544/311; 544/309

[58] Field of Search ............... 544/182, 309, 311, 315, 544/316, 318, 219, 223

[56] References Cited

U.S. PATENT DOCUMENTS 4,470,842  9/1984  Kranz et al. .................... 544/182
4,544,744  10/1985  Schmidt ........................ 544/182
4,578,463  3/1986  Jackman et al. ................ 544/182

Primary Examiner—John M. Ford
Attorney, Agent, or Firm—Sprung Horn Kramer & Woods

[57] ABSTRACT

In the production of an S-substituted isothiourea including the function group

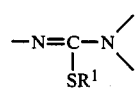

in which $R^1$ is an alkyl, alkenyl, aryl or aralkyl radical, wherein a thiourea including the functional group

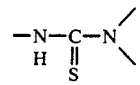

is reacted with an etherifying agent to replace H by $R^1$, the improvement which comprises effecting the reaction in two steps, in the first step reacting the thiourea material with an etherifying agent including the radical R in which R is an alkyl, alkenyl aryl or aralkyl radical different from $R^1$
thereby to produce the ether

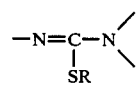

and in the second step reacting the ether with a compound of the formula $R^1SH$. The process is particularly applicable to the production of the known herbicide

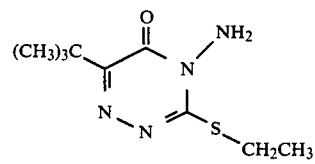

from the corresponding thiourea where in the first step methyl bromide or methyl iodide is used to form the S-methyl isothiourea which is then interchanged with ethyl mercaptan. Higher overall yields and/or economies are thereby achieved.

12 Claims, No Drawings

PRODUCTION OF S-SUBSTITUTED ISOTHIOUREAS

The present invention relates to a process for converting a thiol ether to a thiol or different thiol ether, particularly wherein the starting material is an S-substituted isothiourea.

U.S. Pat. No. 3,671,523 discloses the extremely effective selective herbicide of the formula

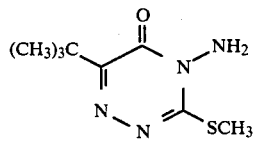

The compound is produced by methylating the corresponding compound having an —SH radical in the 3-position, with a methylating agent such as methyl bromide or methyl iodide, methyl chloride producing much lower yields. While the process works well (with some methylation of the N-2 atom), methyl bromide and iodide are relatively expensive.

U.S. Pat. No. 4,457,774 discloses a similar process for making the compound

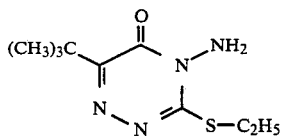

which is also selectively herbicidal, employing ethyl bromide and iodide which are even more expensive than methyl bromide and iodide and produce even lower yields of product.

The art includes disclosures of several other triazinones which carry an S-alkyl substituent in 3-position and other substituents in 4- and 6-positions but, for practical economic considerations, they are produced from expensive alkylating agents reacting with the corresponding 3-thiols.

It is accordingly an object of the present invention to produce other S-substituted isothioureas from S-methyl-substituted isothioureas in a simple inexpensive manner.

It is a further object of the invention to produce thioethers from the corresponding mercaptans in an inexpensive manner.

Still another object of the invention is to convert S-substituted isothioureas to their corresponding thioureas in an inexpensive manner.

These and other objects and advantages of the invention are realized in accordance with the present invention pursuant to which there is provided a process for converting an S-substituted isothiourea including the functional group

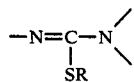

to the corresponding S-substituted isothiourea having the functional group

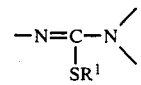

wherein
R is an alkyl, alkenyl, aryl or aralkyl radical, and $R^1$ is hydrogen, or an alkyl, alkenyl, aryl or aralkyl radical, but is different from R, which comprises reacting the starting compound with $R^1SH$ which comprises reacting the starting compound with $R^1SH$.

The process is particularly applicable to starting materials including a heterocyclic ring and especially to those wherein the S-substituted isothiourea structure is part of the ring, e.g. suitably substituted pyrimidines (uracils), 1,3,5-triazines, and the like. Most preferred, however, are starting materials of the formula

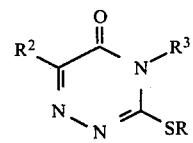

in which
$R^2$ is an alkyl, alkenyl, aryl or aralkyl radical, and $R^3$ is an alkyl, amino or alkylideneimino radical,
particularly those wherein
R is an alkyl or alkenyl radical containing up to 12 carbon atoms or a phenyl, naphthyl or benzyl radical, and $R^1$ is hydrogen, an alkyl or alkenyl radical containing up to 12 carbon atoms or a phenyl, naphthyl or benzyl radical, but is different from R,
$R^2$ is an alkyl or alkenyl radical containing up to 12 carbon atoms, or a phenyl radical, and
$R^3$ is an $NH_2$ radical, or an alkyl, alkenyl, aryl, aralkyl, alkylamino, dialkylamino alkenylamino or arylamino radical containing up to 12 carbon atoms,
and especially those wherein
R is methyl,
$R^1$ is ethyl,
$R^2$ is branched alkyl containing up to 6 carbon atoms, e.g. tert-butyl, fluoro- or chloro-tert.-butyl and branched pentyl containing a quaternary carbon atom, and
$R^3$ is $NH_2$ or alkyl, alkylamino or dialkylamino containing up to 4 carbon atoms, especially $NH_2$ or methyl.

Advantageously the reaction is effected in a solvent and in the presence of a catalyst with removal of by-product RSH as by distillation during or after the reaction, especially where RSH is more volatile than $R^1SH$.

The reaction temperature can range from room temperature or even lower up to the boil, depending upon the solvent employed, but preferably is from about 30° to 100° C.

Suitable solvents include inert organic solvents such as toluene, halogenated hydrocarbons, or the like, but the solvent can also comprise an excess of the reactant mercaptan $R^1SH$ when it is liquid. The use of water is also helpful when the reagent or end product is water-soluble.

Thus, while the reactants can be employed in stoichiometric quantities, large excesses of either of the reactants can be employed, preferably of the less expensive reactant, to drive the reaction to completion.

Advantageously small amounts of acidic or basic materials are employed as catalysts. They can be present in up to stoichiometric amount but as little as 0.001 to about 0.1, preferably about 0.01 to 0.05, mole of catalyst per mole of isothiourea is generally suitable. Basic groups on the reactant molecule can themselves function as internal catalysts. Catalysts are especially useful where low boiling mercaptans containing 1 to 4 carbon atoms, e.g. ethyl mercaptan, are employed. Preferred catalyts include an alkali metal or ammonium hydroxide, an amine, an alkaline imide, an alkali metal alkaline salt or a quaternary ammonium hydroxide, or an acid. Ion exchange resin catalysts can also be employed. Fluoroacetic acid and potassium carbonate are of lesser benefit but DABCO (diazabicyclooctane), triethylamine and methylimidazole were better. Still better were tetramethylammonium hydroxide, the crown ether KF/18-Crown 6 and NaOH but the best results were obtained with KOH.

As noted, if $R^1SH$ is hydrogen sulfide and is employed in excess by bubbling into a solution of isothiourea, it is also possible to form the thiol or mercaptan, i.e. to convert —SR to —SH.

In accordance with another aspect of the invention there is provided a two step process for going from the thiourea

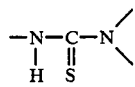

to the isothiourea

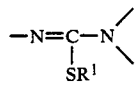

by first etherifying to convert=S or its isomer —SH to —SR and then reacting with $R^1SH$ to produce —$SR^1$.

While not limited thereto, the invention is especially useful in replacing an ether group to produce the following compounds in addition to those exemplified hereinbelow:

1-amino-6-ethylthio-3-(2,2-dimethylpropyl)-1,3,5-triazine-2,4(1H,3H)-dione
  4-amino-6-chloro-tert.-butyl-3-propargylthio-1,2,4-triazine-5-one
  4-amino-6-fluoro-tert.-butyl-3-allylthio-1,2,4-triazin-5-one
  4-amino-6-fluoro-tert.-butyl-3-methylthio-1,2,4-triazin-5-one
  4-amino-6-(1,1-bis-fluoromethyl-ethyl)-3-buten-2-ylthio-1,2,4-triazin-5-one
  4-amino-6-ethoxy-tert.-butyl-3-propargylthio-1,2,4-triazin-5-one
  6-(2,3-dimethyl-but-2-yl)-4-methyl-3-methylthio-1,2,4-triazin-5-one
  4-amino-6-cyclobutyl-3-methylthio-1,2,4-triazin-5-one
  6-cyclobutyl-4-isopropylideneamino-3-methylthio-1,2,4-triazin-5-one.

The invention will be further described with reference to the following illustrative examples wherein all parts are by weight unless otherwise expressed:

EXAMPLE 1

A mixture of 230 g (1 mole of 93% active ingredient) of 4-amino-6-t-butyl-3-methylthio-1,2,4-triazin-5-one and 310 g (5 moles) of ethyl mercaptan and 0.5 g of crushed solid KOH was stirred and refluxed onto a 10° C. condenser. The vapors which pass through the condenser (methyl and ethyl mercaptans) were collected in a dry ice or caustic trap. The reaction was continued until thin layer chromatography indicated that the starting material was gone (usually 2–8 hours). The unreacted ethyl mercaptan was then distilled off while ~600 ml of warm (40° C.) water was added at such a rate that the water addition was complete when ~⅓ of the mercaptan had distilled. Distillation was continued until ~100 ml of water distilled at 100° C. The solution was then allowed to cool with rapid stirring. The product crystallized at 60°–70° C. and at 20° C. was filtered and washed with water, then dried. The final product, 4-amino-6-t-butyl-3-ethylthio-1,2,4-triazin-5-one, was obtained in nearly quantitative yield and contained less than 1% of the starting 3-methylthio compound.

EXAMPLE 2

A solution of 2.14 g (0.01 mole) of 4-amino-6-t-butyl-3-methylthio-1,2,4-triazin-5-one and 1 drop of triethylamine in 25 ml of toluene was treated with excess $H_2S$ gas for 0.5 hours. The corresponding 3-thio compound was produced in quantitative yield.

EXAMPLE 3

10 g (0.0514 mole) of 4-amino-6-t-butyl-3-methylthio-1,2,4-triazin-5-one, 35 g (0.257 mole) of m-thiocresol, and 0.2 g of potassium hydroxide were refluxed in absolute ethanol for 8 hours. The product, 4-amino-6-t-butyl-3-($3^1$-methylphenylthio)-1,2,4-triazin-5-one, was obtained by crystallization from ethanol-water (m.p. 150°–3°).

EXAMPLE 4

A mixture of 10.7 g (0.05 mole) of 4-amino-6-t-butyl-3-methylthio-1,2,4-triazin-5-one and 35 g (0.17 mole) of dodecanethiol was heated at 120° C. for 8 hours with a gentle nitrogen sweep. Cyclohexane was added and the product (4-amino-6-t-butyl-3-dodecylthio-1,2,4-triazin-5-one) crystallized in nearly quantitative yield, m.p. 64°–66° C.

EXAMPLE 5

4-amino-6-methyl-3-methylthio-1,2,4-triazin-5-one (8.6 g, 0.05 mole) t-butylmercaptan (27 g, 0.3 mole), and 1.5 g of 20% tetramethylammonium hydroxide were refluxed for 60 hours. The solution was evaporated to dryness, 35 ml of hexane at 60° C. was added forming a solution, it was cooled to room temperature producing a crop of 7.5 g (70%) of the corresponding 3-t-butylthio compound, m.p. 124°–125° C. Additional product remained in the mother liquor.

EXAMPLE 6

2-methylthio-3-amino-6-methyluracil (1.1 g, 0.0064 mole), dodecanethiol (10 g, 0.0495 mole), and a few drops of tetramethylammonium hydroxide solution (25%) were heated at 140° C. for 3 hours. Dilution with heptane (30 ml) and cooling gave 1.7 g (80% yield) of the product, 2-dodecylthio-3-amino-6-methyluracil, m.p. 80° C.

The reaction is illustrated as follows:

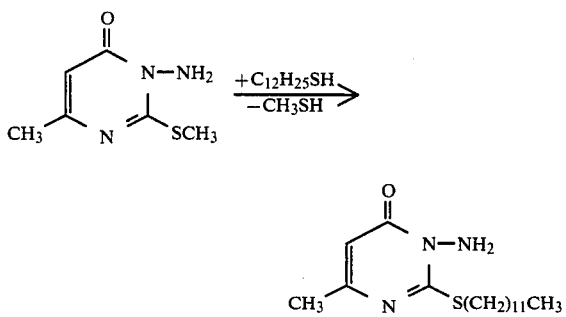

EXAMPLE 7

1-amino-3(2,2-dimethylpropyl)-6-ethylthio-1,3,5-triazine-2,4(1H, 3H)dione (5 g, 0.019 mole), cyclohexanethiol (6.0 g, 0.05 mole) and 2 drops of tetramethylammonium hydroxide solution (25%) were heated at 150° C. for 4 hours. Heptane (20 ml) was added slowly and 5.7 g (94%) of the product 1-amino-3(2,2-dimethylpropyl)-6-cyclohexylthio-1,3,5-triazine-2,4(1H, 3H)dione was obtained by filtration. The reaction is illustrated as follows:

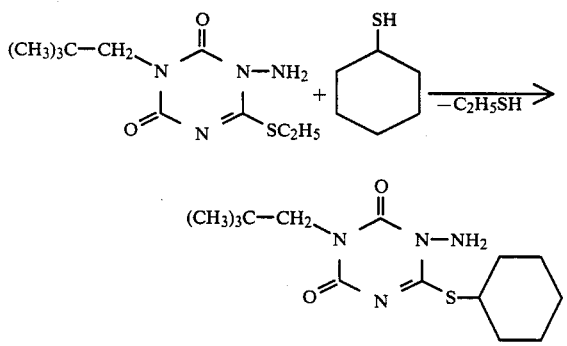

It will be understood that the specification and examples are illustrative but not limitative of the present invention and that other embodiments within the spirit and scope of the invention will suggest themselves to those skilled in the art.

We claim:

1. A process for converting a triazine or pyrimidine containing in the ring an S-substituted isothioura group of the formula

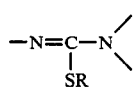

to the corresponding triazine or pyrimidine containing in the ring an S-substituted isothiourea group of the formula

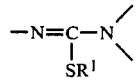

wherein
R is an alkyl, alkenyl, aryl or aralkyl radical, and
$R^1$ is hydrogen, or an alkyl, alkenyl, aryl or aralkyl radical, but is different from R,
which comprises reacting the starting compound with $R^1SH$.

2. A process according to claim 1, wherein the starting compound is of the formula

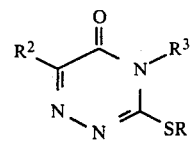

in which
$R^2$ is an alkyl, alkenyl, aryl or aralkyl radical and
$R^3$ is an alkyl, amino or alkylideneimino radical.

3. A process according to claim 1, wherein the reaction is effected in the presence of a solvent.

4. A process according to claim 3, wherein during or after the reaction by-product of the formula RSH is distilled off from the principal product.

5. A process according to claim 1, wherein the reaction is effected in the presence of a catalyst.

6. A process according to claim 5, wherein the catalyst comprises an alkali metal or ammonium hydroxide, an amine, an alkaline imide, an alkal metal alkaline salt or a quaternary ammonium hydroxide, or an acid.

7. A process according to claim 1, wherein the reaction is effected in the presence of potassium hydroxide as catalyst.

8. A process according to claim 2, in which
R is alkyl of 1 to 12 carbon atoms,
$R^1$ is hydrogen, or alkyl of 1 to 12 carbon atoms, but is different from R,
$R^2$ is an alkyl radical of up to 6 carbon atoms or phenyl, optionally substituted by halogen and/or $C_{1-4}$-alkoxy, and
$R^3$ is an amino, alkyl, alkylamino, dialkylamino or alkylideneimino radical each containing up to 6 carbon atoms.

9. A process according to claim 4, wherein RSH is more volatile than $R^1SH$.

10. A process according to claim 8, wherein the starting compound is of the formula

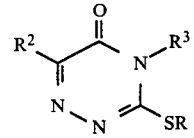

in which
R is methyl, and
$R^2$ is branched alkyl containing up to 6 carbon atoms or phenyl each optionally including a halogen atom.

11. A process according to claim 10, in which:
$R^2$ is tert.-butyl, and
$R^3$ is $-NH_2$.

12. A process according to claim 11, wherein the reaction is effected in excess ethyl mercaptan as solvent in the presence of potassium hydroxide, and by-product $CH_3SH$ is distilled off during or after the reaction.

* * * * *